(12) United States Patent
Chang et al.

(10) Patent No.: US 11,471,585 B2
(45) Date of Patent: Oct. 18, 2022

(54) NEGATIVE PRESSURE WOUND THERAPY DEVICE, SYSTEM AND METHOD

(71) Applicant: XIAMEN SUNEETEK MEDICAL EQUIPMENT CO., LTD., Xiamen (CN)

(72) Inventors: Po-Han Chang, New Taipei (TW); Shih Hua Hsiao, New Taipei (TW); Bo Cheng Huang, New Taipei (TW); Chi Yuan Chen, New Taipei (TW); Ting Hsuan Chung, New Taipei (TW)

(73) Assignee: XIAMEN SUNEETEK MEDICAL EQUIPMENT CO., LTD., Xiamen (CN)

( * ) Notice: Subject to any disclaimer, the term of this patent is extended or adjusted under 35 U.S.C. 154(b) by 563 days.

(21) Appl. No.: 16/212,369

(22) Filed: Dec. 6, 2018

(65) Prior Publication Data

US 2019/0201599 A1    Jul. 4, 2019

(30) Foreign Application Priority Data

Dec. 29, 2017 (CN) .......................... 201711497896.9

(51) Int. Cl.
  *A61M 1/00* (2006.01)
(52) U.S. Cl.
  CPC ............ *A61M 1/90* (2021.05); *A61M 1/0001* (2013.01); *A61M 1/60* (2021.05); *A61M 1/743* (2021.05);
  (Continued)
(58) Field of Classification Search
  CPC .................... A61M 1/0023; A61M 2205/3382
  See application file for complete search history.

(56) References Cited

U.S. PATENT DOCUMENTS

| 6,142,982 A * | 11/2000 | Hunt ..................... A61M 27/00 604/313 |
| 8,827,983 B2 * | 9/2014 | Braga .................. G01F 23/241 604/540 |

(Continued)

FOREIGN PATENT DOCUMENTS

| CN | 1938805 A | 3/2007 |
| CN | 102160904 A | 8/2011 |

(Continued)

OTHER PUBLICATIONS

Office Action issued in corresponding Chinese Application No. 201711497896.9, dated Feb. 3, 2021, with English machine translation.

*Primary Examiner* — Catharine L Anderson
*Assistant Examiner* — Arjuna P Chatrathi
(74) *Attorney, Agent, or Firm* — Juan Carlos A. Marquez; Marquez IP Law Office, PLLC (57) ABSTRACT

The present invention relates to a negative pressure wound therapy device, system and method. The negative pressure wound therapy device is connected with a dressing, and comprises a housing, a control circuit board, a pump, and an aspiration conduit. The pump generates negative pressure. The pump may comprise a voltage-actuated deformation element (such as piezoelectric vibration element) to push fluid from an aspiration end to a discharge end. The aspiration conduit has a pump end and a dressing end. The pump end is fluidly connected to the aspiration end of the pump, and the dressing end is fluidly connected to the dressing used for covering a wound. The control circuit board is disposed in the housing, controls the pump to generate the negative pressure in the aspiration conduit, and applies negative pressure to the wound covered by the dressing via the aspiration conduit.

9 Claims, 9 Drawing Sheets

(52) U.S. Cl.
CPC ............... *A61M 1/78* (2021.05); *A61M 1/80* (2021.05); *A61M 1/73* (2021.05); *A61M 1/82* (2021.05); *A61M 2205/3331* (2013.01); *A61M 2205/3337* (2013.01); *A61M 2205/3382* (2013.01); *A61M 2205/587* (2013.01); *A61M 2205/75* (2013.01); *A61M 2205/8206* (2013.01); *A61M 2209/088* (2013.01)

(56) References Cited

U.S. PATENT DOCUMENTS

| | | | | |
|---|---|---|---|---|
| 2010/0191199 | A1* | 7/2010 | Evans | A61M 1/73 604/319 |
| 2011/0112492 | A1* | 5/2011 | Bharti | A61F 13/0216 604/319 |
| 2011/0288510 | A1* | 11/2011 | Locke | A61M 1/74 604/319 |
| 2012/0184932 | A1* | 7/2012 | Giezendanner | A61M 1/80 604/319 |
| 2013/0237937 | A1* | 9/2013 | Ramella | A61M 1/0001 604/319 |
| 2013/0267918 | A1* | 10/2013 | Pan | A61M 1/90 604/318 |
| 2013/0304007 | A1* | 11/2013 | Toth | A61M 1/78 604/321 |
| 2017/0112974 | A1* | 4/2017 | Fujisaki | A61M 1/80 |

FOREIGN PATENT DOCUMENTS

| | | |
|---|---|---|
| CN | 102294075 A | 12/2011 |
| CN | 105492035 A | 4/2016 |
| CN | 106286241 A | 1/2017 |
| WO | 2017192810 A1 | 11/2017 |

* cited by examiner

FIG. 10

NEGATIVE PRESSURE WOUND THERAPY DEVICE, SYSTEM AND METHOD

BACKGROUND OF THE INVENTION

1. Field of the Invention

The present invention relates to a wound therapy device, a wound therapy system and a wound therapy method, and more particularly to a negative pressure wound therapy device connected with a dressing, a negative pressure wound therapy system and a negative pressure wound therapy method.

2. Description of the Related Art

In traditional clinical therapy, many acute and chronic wounds would take a long time to heal, thereby inconveniencing and affecting the quality of life of the patient. With progress in science and technology, various manners for accelerating wound healing have been developed, among which negative pressure wound therapy (NPWT) is clinically proved to effectively accelerate wound healing and has been widely applied to wound therapy. Negative pressure wound therapy mainly refers to: applying a negative pressure to a wound by means of a special dressing such as porous open-cell polyurethane (PU) foam, aspirating pus from the wound, and maintaining the wound in an appropriate wet environment, so as to alleviate edemas of surrounding tissues, to stimulate proliferation of granulation tissues and to thus accelerate wound healing. In addition, such special dressing can reduce the problem of sticking to the wound so as to effectively isolate the wound from bacteria, and provides a micro-acid environment to reduce a risk of wound infection.

However, the currently known negative pressure wound therapy device is so expensive that an ordinary patient nursed at home cannot afford it, so it is applicable only to a hospital environment under most circumstances. In addition, because the currently known negative pressure wound therapy device is large and needs to be externally connected with a power supply, the known negative pressure wound therapy device cannot be carried, so the patient cannot leave the sickbed to act freely, thereby limiting the activity range of the patient.

Therefore, it is urgently necessary to provide, for the industry, a portable negative pressure wound therapy device, which not only has a fair price, but also can be used by a patient at home to improve the patient's quality of life.

SUMMARY OF THE INVENTION

In a preferable embodiment, the present invention provides a negative pressure wound therapy device connected with a dressing. The device comprises a housing, a control circuit board, a pump, and an aspiration conduit. The pump is disposed in the housing, and comprises a discharge end and an aspiration end. The pump discharges fluid from the discharge end to generate negative pressure at the aspiration end. The pump further comprises a voltage-actuated deformation element to push the fluid from the aspiration end to the discharge end. The aspiration conduit has a pump end and a dressing end. The pump end is fluidly connected to the aspiration end of the pump, and the dressing end is fluidly connected to the dressing used for covering a wound. The control circuit board is disposed in the housing, controls the pump to generate the negative pressure in the aspiration conduit, and applies negative pressure to the wound covered by the dressing via the aspiration conduit.

In another preferable embodiment, the negative pressure wound therapy device further comprises a canister for storing liquid aspirated from the wound. The canister has a top for engaging with the housing, and has a first end for connecting with the dressing end of the aspiration conduit. The canister has a second end for connecting with a dressing conduit of the dressing. The canister comprises at least one liquid-full probe extending inwardly from a top wall of the canister, and the at least one liquid-full probe generates a liquid-full signal to the control circuit board when the at least one liquid-full probe contacts the liquid aspirated from the wound.

In another preferable embodiment, the canister further comprises at least one liquid blocking structure surrounding the at least one liquid-full probe and having an opening facing a side wall of the canister, so when the negative pressure wound therapy device is tilted, the liquid aspirated from the wound only contacts the at least one liquid-full probe from the opening of the at least one liquid blocking structure to prevent the at least one liquid-full probe from generating the liquid-full signal incorrectly.

In another preferable embodiment, the at least one liquid-full probe respectively comprises a first liquid-full probe adjacent to a first side wall of the canister and a second liquid full-probe adjacent to a second wall of the canister opposite to the first side wall. The at least one liquid blocking structure respectively comprises a first liquid blocking structure surrounding the first liquid-full probe and a second liquid blocking structure surrounding the second liquid-full probe. The openings of the first liquid blocking structure and the second liquid blocking structure respectively face the first side wall and the second side wall of the canister.

In another preferable embodiment, the first liquid-full probe and the second liquid-full probe are electrically conductive to each other to generate the liquid-full signal when the first liquid-full probe and the second liquid-full probe simultaneously contact the liquid.

In another preferable embodiment, the negative pressure wound therapy device further comprises a first terminal and a second terminal disposed at the bottom of the housing. The first terminal and the second terminal electrically connect the first liquid-full probe and the second liquid-full probe to the control circuit board respectively.

In another preferable embodiment, the aspiration conduit comprises a check valve disposed between the pump end and the dressing end of the aspiration conduit. The check valve prevents the fluid from flowing to the dressing end from the pump end of the aspiration conduit.

In another preferable embodiment, the negative pressure wound therapy device further comprises a snuffle valve. The aspiration conduit comprises a tee conduit with a first end, a second end and a third end. The first end of the tee conduit is fluidly connected to the check valve, the second end of the tee conduit is fluidly connected to the dressing end of the aspiration conduit, and the third end of the tee conduit is fluidly connected to the snuffle valve. The snuffle valve is controlled by the control circuit board to release the negative pressure in the aspiration conduit.

In another preferable embodiment, the housing is water-resistant.

In another preferable embodiment, the present invention provides a negative pressure wound therapy system, comprising the negative pressure wound therapy device and the dressing connected with the negative pressure wound therapy device, wherein the dressing is used for covering the wound.

In another preferable embodiment, the present invention provides a negative pressure wound therapy method, comprising: providing the negative pressure wound therapy device; connecting the dressing to the dressing end of the negative pressure wound therapy device; covering the wound with the dressing; and setting an operating parameter of the negative pressure wound therapy device.

To facilitate further understanding and implementation of the technical features of the present invention, detailed description will be given in conjunction with the following embodiments and drawings. The description only concerns preferable embodiments of the present invention, not limitations in any form. Any modifications or changes made under the same spirit of the present invention fall within the scope of protection of the present invention.

BRIEF DESCRIPTION OF THE DRAWINGS

The invention will be described according to the appended drawings, in which.

PREFERRED EMBODIMENT OF THE PRESENT INVENTION

Figure 1A:
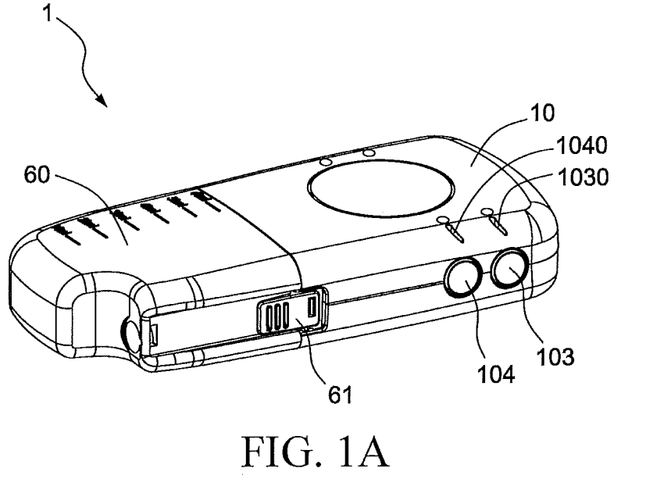
FIG. 1A is a perspective view of a negative pressure wound therapy device of the present invention.
Figure 1B:
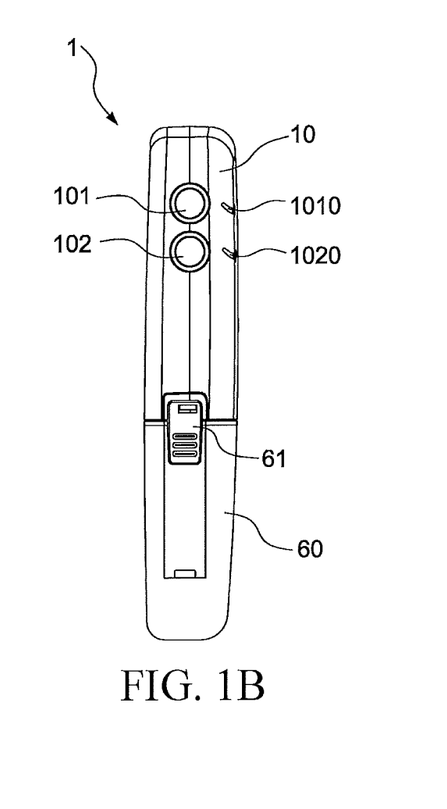
FIG. 1B is a left view of a negative pressure wound therapy device of the present invention.
Figure 2:
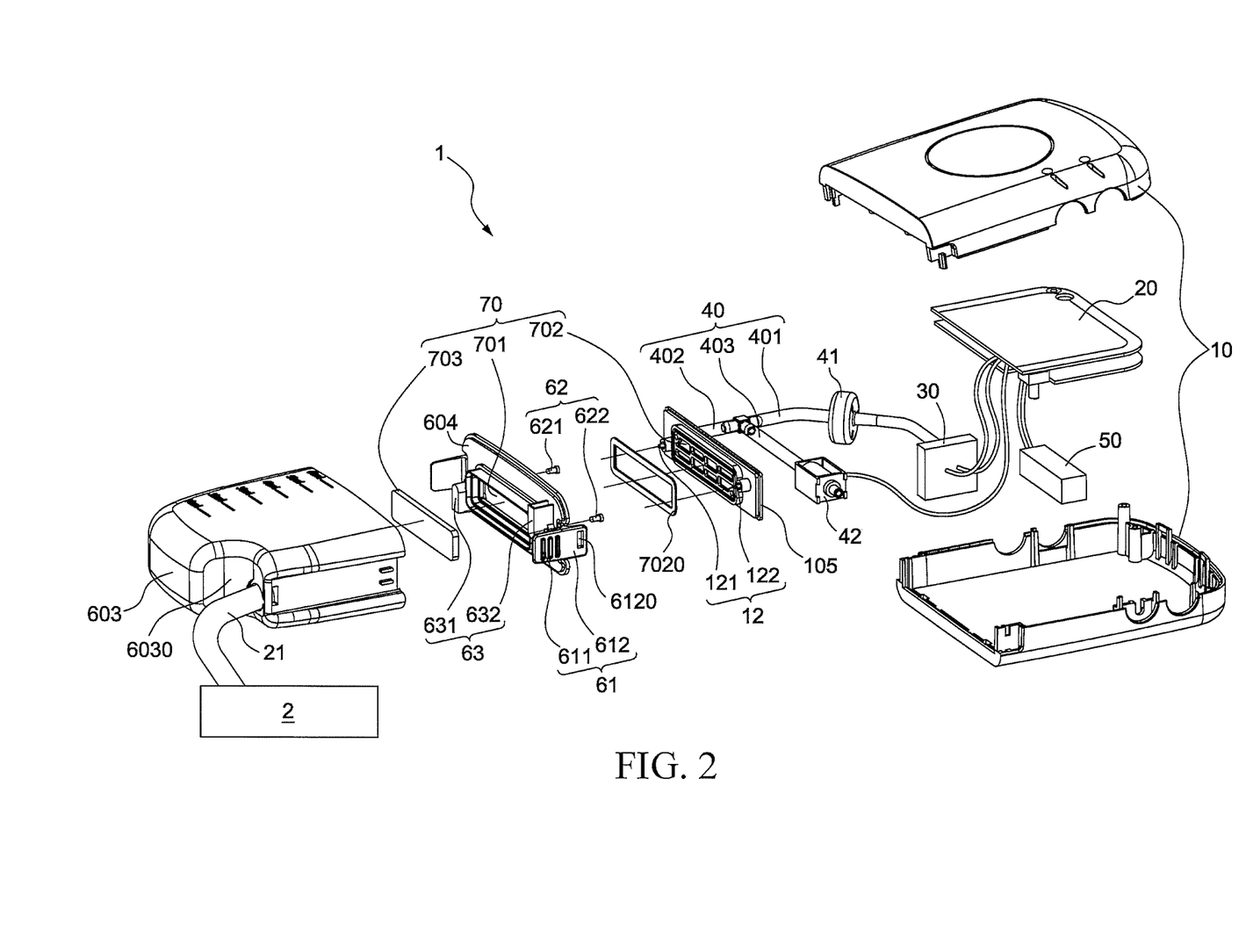
FIG. 2 is an exploded view displaying main elements of a negative pressure wound therapy device of the present invention.

Please refer to FIG. 1A, FIG. 1B and FIG. 2. FIG. 1A is a perspective view of a negative pressure wound therapy device 1 of the present invention. FIG. 1B is a left view of a negative pressure wound therapy device of the present invention. FIG. 2 is an exploded view displaying main elements of a negative pressure wound therapy device 1 of the present invention. The negative pressure wound therapy device 1 comprises a housing 10, a control circuit board 20, a pump 30, an aspiration conduit 40, a power device 50, and a canister 60.

Buttons and indicator lights are disposed on the surface of the housing 10, and are electrically connected to the control circuit board 20 disposed in the housing 10, respectively. In a specific embodiment of the present invention, a power button 103 and a standby button 104 are disposed on the left side of the housing 10, and a power indicator light 1030 and a standby indicator light 1040 are respectively disposed at positions, close to the power button 103 and the standby button 104, on the front surface of the housing 10. A pressure button 101 and a mode button 102 are disposed on the right side of the housing 10, and a pressure indicator light 1010 and a mode indicator light 1020 are respectively disposed at positions, close to the pressure button 101 and the mode button 102, on the front surface of the housing 10. The button and indicator light positions of the housing 10 satisfy human factor engineering design. When a user holds the negative pressure wound therapy device 1 in a single hand, buttons are approximately located at positions that may be touched by a thumb and index finger, for operation and use by the user. It is noted that the button and indicator light positions of the housing 10 are not limited to the above-mentioned positions, and may be appropriately adjusted according to practical design requirements. In addition, in a specific embodiment of the present invention, the housing 10 is made water-resistant by glue, and has waterproof and dustproof effects such as the level of IP22.

The pump 30 is disposed in the housing 10, and is electrically connected with the control circuit board 20 disposed in the housing 10. The pump 30 defines an aspiration end and a discharge end in the direction of fluid flow. The pump 30 discharges the fluid from the aspiration end to the discharge end to generate negative pressure at the aspiration end.

The aspiration conduit 40 has a pump end and a dressing end, wherein the pump end is fluidly connected to the aspiration end of the pump 30, and the dressing end is fluidly connected to a dressing 2 used for covering a wound. In a specific embodiment of the present invention as shown in FIG. 2, the dressing end of the aspiration conduit 40 is connected to the canister 60. In a preferable embodiment of the present invention, the aspiration conduit 40 comprises a check valve 41 disposed between the pump end and the dressing end. The check valve 41 prevents the fluid from flowing to the dressing end from the pump end of the aspiration conduit 40. In a preferable embodiment, the aspiration conduit 40 further comprises a tee conduit with a first end 401, a second end 402 and a third end 403. The first end 401 of the tee conduit is fluidly connected to the check valve 41, the second end 402 of the tee conduit is fluidly connected to the dressing end of the aspiration conduit 40, and the third end 403 of the tee conduit is fluidly connected to a snuffle valve 42. The snuffle valve 42 is electrically connected with the control circuit board 20 and is controlled by the control circuit board 20 to release the negative pressure in the aspiration conduit 40 as required.

In a specific embodiment of the present invention as shown in FIG. 2, the negative pressure wound therapy device 1 comprises a canister 60. The canister 60 has a top (a top surface 604 of a canister as shown in FIG. 2) for engaging with the housing 10. The canister 60 has a first end and a second end. The first end, located on the top surface 604 of the canister, of the canister 60 is connected with the dressing end of the aspiration conduit 40, and the second end on a bottom surface 603 of the canister 60 is connected with a dressing conduit 21 of the dressing 2. In a specific embodiment of the present invention, a filter member 70 is disposed at a junction between the canister 60 and the dressing end of the aspiration conduit 40, and may prevent liquid in the canister 60 from flowing back to the dressing end of the aspiration conduit 40. In other embodiments of the present invention, the filter member 70 has a first filter member 701 and a second filter member 702. The first filter member 701 is disposed on the top surface 604 of the canister 60, and the second filter member 702 is disposed on a bottom surface 105 of the housing 10. By means of the first filter member 701 and the second filter member 702, the liquid in the canister 60 may be prevented from flowing back to the dressing end of the aspiration conduit 40. Moreover, when the canister 60 is separated from the housing 10, the liquid in the canister 60 may be prevented from leaking by means of the first filter member 701. In other embodiments of the present invention, an activated carbon surface 703 may be disposed on a surface, facing the canister, of the first filter member 701, for further filtration. In addition, in a specific embodiment of the present invention, when the canister 60 is combined with the housing 10, in order to prevent the liquid from leaking from a junction between the canister 60 and the housing 10, a rubber gasket 7020 is disposed at a junction between the bottom surface 105 of the housing 10 and the top surface 604 of the canister to increase the tightness of the junction. In a specific embodiment of the present invention, a recess 6030 is disposed between the second end, located on the bottom surface 603 of the reservoir, of the canister 60 and the dressing conduit 21, so that when the dressing conduit 21 is connected to the second end of the canister 60, a connecting end of the dressing conduit 21 cannot protrude from the bottom surface 603 of the canister 60, thereby reducing disengagement of the dressing conduit 21 caused by collision against the canister 60.

Figure 3A:
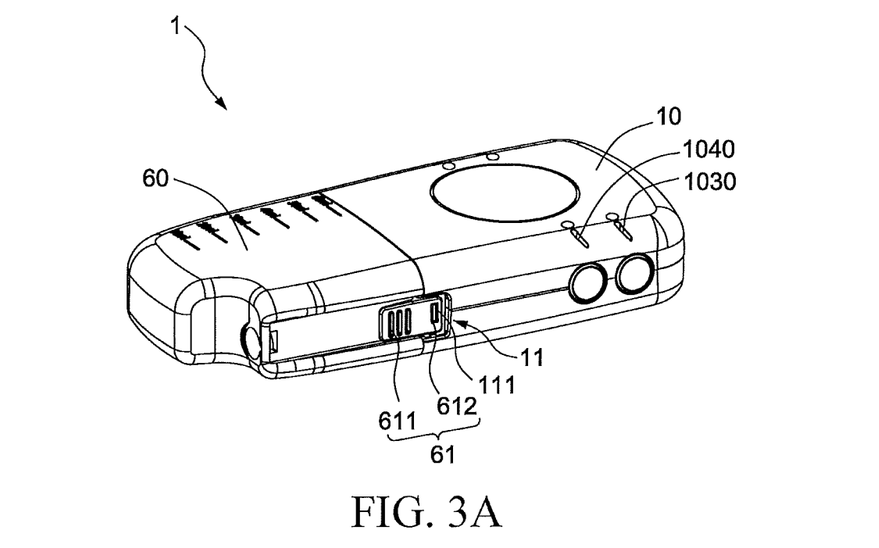
FIG. 3A and FIG. 3B are schematic diagrams of a disassembled liquid canister of a negative pressure wound therapy device of the present invention.
Figure 3B:
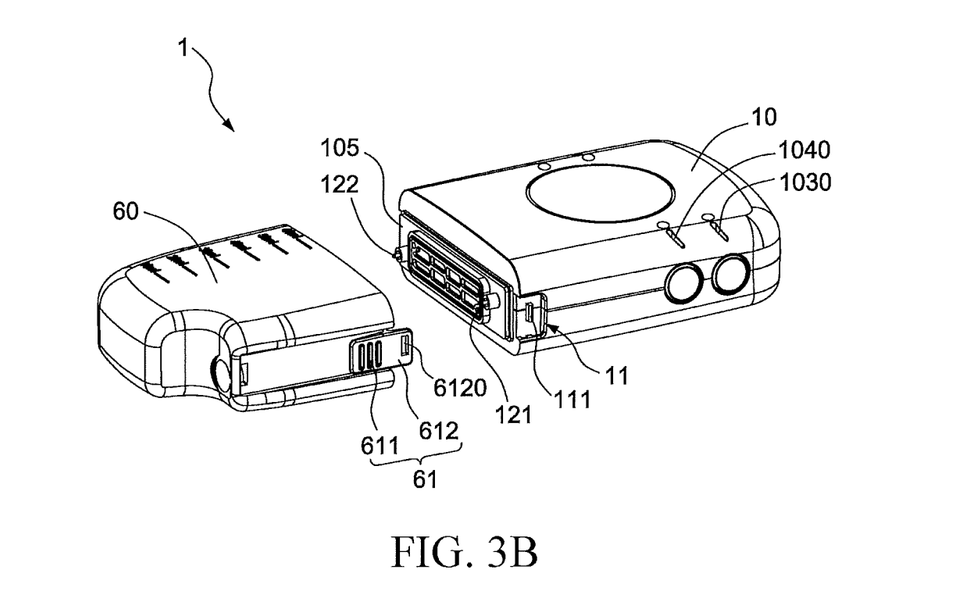

Please refer to FIG. 3A and FIG. 3B. FIG. 3A and FIG. 3B show schematic diagrams of a disassembled canister 60 of a negative pressure wound therapy device 1 of the present invention. The top of the canister 60 is provided with a fixed member 61 for engaging with a fixed member 11 at a position corresponding to the bottom of the housing 10, so that the top of the canister 60 may be connected to the bottom of the housing 10. See FIG. 3B. In a specific embodiment of the present invention, the lower portion of the fixed member 61 of the canister 60 is a pressing portion 611, and the upper portion is a fastening portion 612. The fastening portion 612 has a recess hole 6120 corresponding to a protruding portion 111 of the fixed member 11 of the housing 10, so that when the canister 60 engages with the housing 10, the protruding portion 111 of the housing 10 may penetrate through the recess hole 6120 of the fastening portion 612 of the canister 60 (as shown in FIG. 3A). When a user desires to separate the canister 60 from the housing 10, the user may press the pressing portion 611 of the canister 60, so the recess hole 6120 of the canister 60 disengages from the protruding portion 111 of the housing 10 and does not engage therewith, the canister 60 then moves down, and therefore the canister 60 is separated from the housing 10 (as shown in FIG. 3B). In a specific embodiment of the present invention, the recess hole 6120 of the canister 60 is strip-shaped, and the protruding portion 111 of the housing 10 corresponds to the recess hole 6120 of the canister 60 in shape. In other embodiments of the present invention, the shape of the recess hole 6120 of the canister 60 and the shape of the protruding portion 111 of the housing 10 are not limited to a strip shape, and may be adjusted to circle, oval, square or other shapes as demanded. In addition, in a specific embodiment of the present invention, there are two fixed members 61 of the canister 60, respectively disposed on the left side and the right side of the top of the canister 60, and two fixed members 11 at the corresponding positions of the housing 10, thereby providing an enhanced fastening effect.

Figure 4:
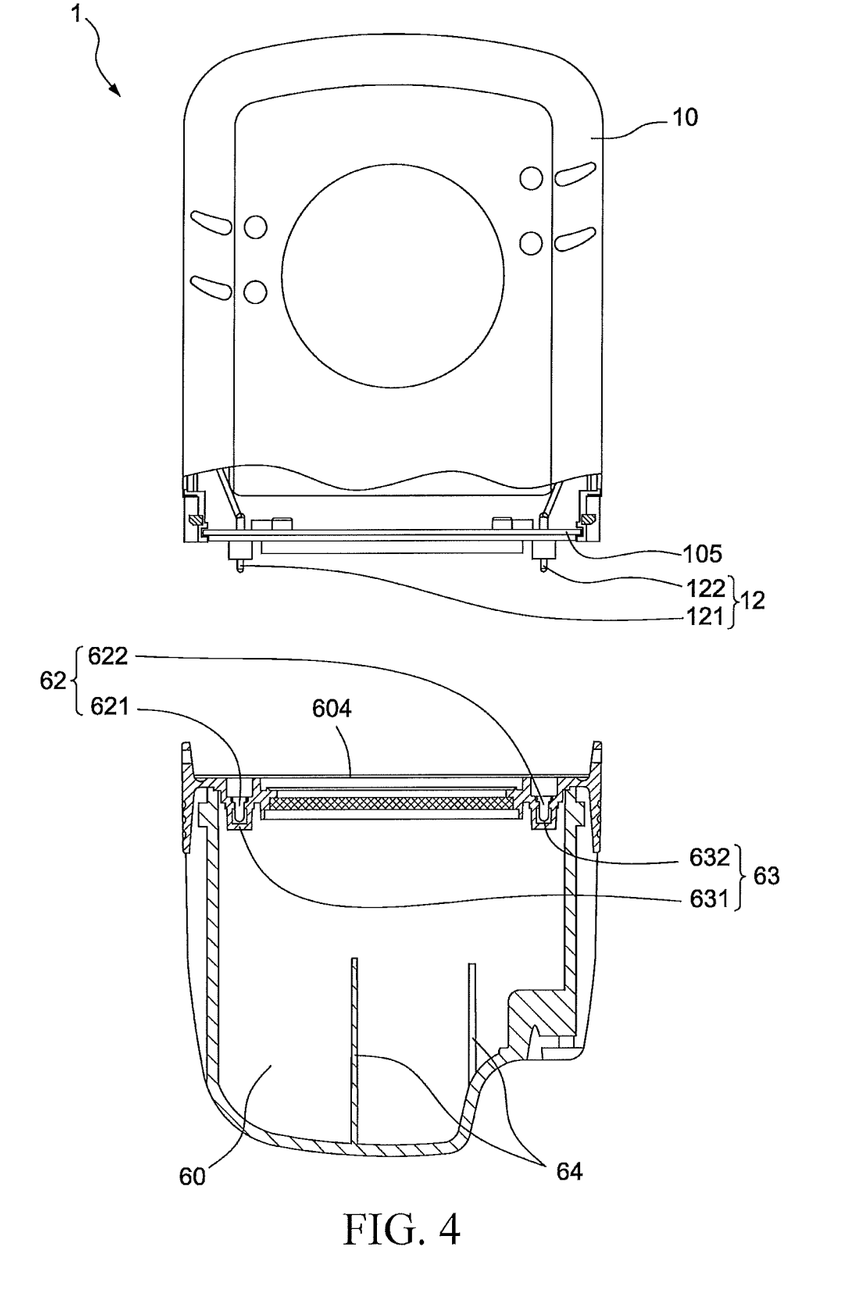
FIG. 4 is a partial sectional view of a negative pressure wound therapy device of the present invention.
Figure 5A:
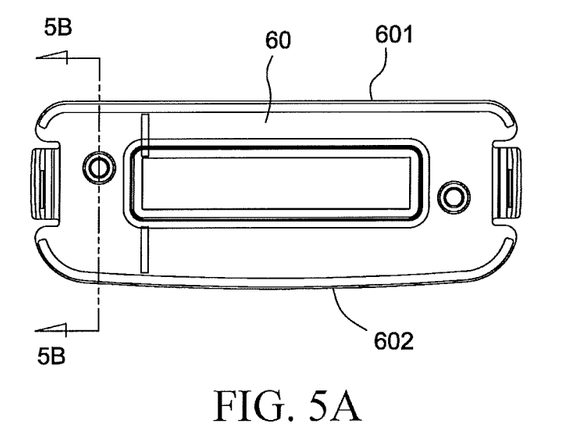
FIG. 5A is a schematic diagram of liquid detection when a canister of a negative pressure wound therapy device of the present invention is tilted forwards.
Figure 5B:
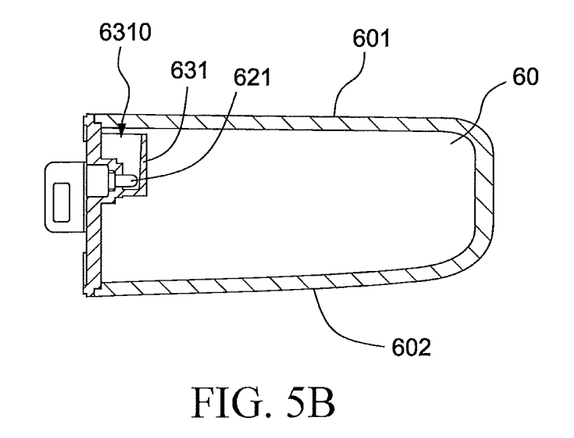
FIG. 5B is a sectional view of FIG. 5A.
Figure 5C:
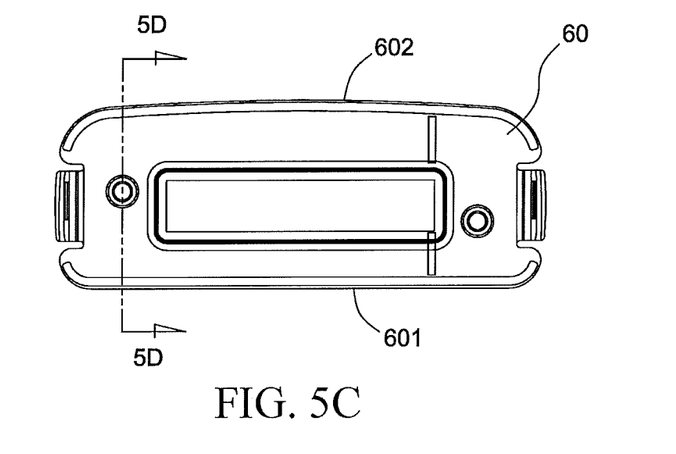
FIG. 5C is a schematic diagram of liquid detection when a canister of a negative pressure wound therapy device of the present invention is tilted backwards.
Figure 5D:
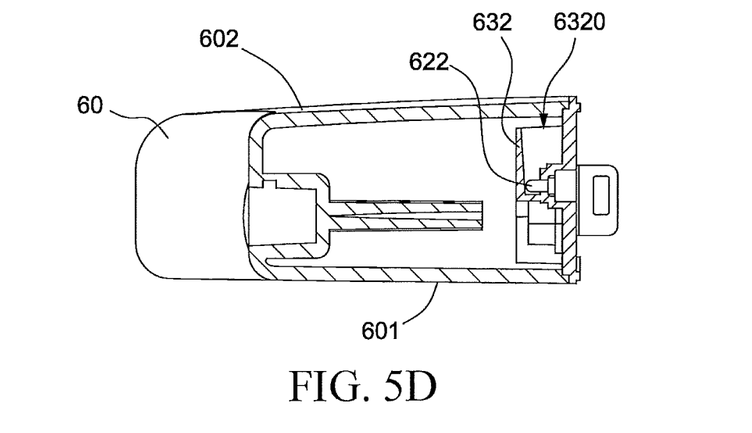
FIG. 5D is a sectional view of FIG. 5C.

Please refer to FIG. 4 and FIG. 5A to FIG. 5D. FIG. 4 shows a sectional view of a negative pressure wound therapy device 1 of the present invention. FIG. 5A is a schematic diagram of liquid detection when a canister 60 of a negative pressure wound therapy device 1 of the present invention is tilted forwards. FIG. 5B is a sectional view of FIG. 5A. FIG. 5C is a schematic diagram of liquid detection when a canister 60 of a negative pressure wound therapy device 1 of the present invention is tilted backwards. FIG. 5D is a sectional view of FIG. 5C. In order to detect the quantity of liquid in the canister 60, the canister 60 is provided with a liquid-full probe 62 extending inwardly from a top wall of the defined top surface 604 of the canister 60, so that the bottom of the liquid-full probe 62 is located in the canister 60, the top of the liquid-full probe 62 is located on a top wall of the defined top surface 604 of the canister 60, and the liquid-full probe may be electrically connected with a terminal 12 at a position corresponding to the bottom surface 105 of the housing 10 so as to electrically connect to the control circuit board 20 as shown in FIG. 2. When the liquid-full probe 62 contacts liquid such as human tissue liquid or blood in the canister 60, the liquid-full probe 62 generates a liquid-full signal to the control circuit board 20 via the terminal 12 of the housing, thereby stopping action of the pump 30 and presenting an alarm. In a specific embodiment, the housing 10 has a protruding terminal 12 capable of telescopically moving between a first state (extension state) and a second state (retraction state), for detecting whether the canister 60 is actually fastened with the housing 10. When the canister 60 is not fastened with the housing 10, the terminal 12 is in the first state (extension state). In this case, the liquid-full probe 62 is not electrically connected with the terminal 12 of the housing 10, and the pump 30 is in an actuated state. When the canister 60 is fastened with the housing 10, the terminal 12 is pressed by the liquid-full probe 62 of the canister 60 to be in the second state (retraction state). In this case, the liquid-full probe 62 is electrically connected with the terminal 12 of the housing 10. In a specific embodiment of the present invention, the liquid-full probe 62 comprises a first liquid-full probe 621 adjacent to a first side wall 601 of the canister 60 and a second liquid full-probe 622 adjacent to a second wall 602 opposite to the first side wall 601, wherein the first liquid-full probe and the second liquid-full probe are respectively located on the top surface 604 of the canister 60. Therefore, the first liquid-full probe 621 and the second liquid full-probe 622 are not in the same horizontal plane when the canister 60 is tilted forwards or backwards. The terminal 12 on the bottom surface 105 of the bottom of the housing 10 has a first terminal 121 and a second terminal 122, corresponding to the first liquid-full probe 621 and the second liquid full-probe 622, and the first terminal 121 and the second terminal 122 electrically connect the first liquid-full probe 621 and the second liquid full-probe 622 respectively to the control circuit board 20. When the liquid such as human tissue liquid or blood aspirated in the canister 60 simultaneously contacts the first liquid-full probe 621 and the second liquid full-probe 622, the first liquid-full probe 621 and the second liquid-full probe 622 are electrically conductive to each other to generate the liquid-full signal to the control circuit board 20 via the first terminal 121 and the second terminal 122 of the housing 10. Because the first liquid-full probe 621 and the second liquid-full probe 622 are respectively located at two opposite ends of the top surface 604 of the canister 60, the accuracy of liquid-full detection may be enhanced. In other embodiments of the present invention, the number of liquid-full probes 62 is not limited to one or two; instead, an appropriate number may be selected as demanded, and the positions of the liquid-full probes 62 may also be adjusted as demanded.

When the negative pressure wound therapy device 1 is accidentally tilted, the liquid in the canister 60 may contact the liquid-full probe 62 prematurely and cause misjudgment. In order to improve the detection accuracy of the quantity of the liquid in the canister 60, the canister 60 further comprises a liquid blocking structure 63 surrounding the liquid-full probe 62 and having an opening facing a side wall of the canister 60. When the negative pressure wound therapy device 1 is tilted, the liquid aspirated from the wound in the canister 60 only contacts the liquid-full probe 62 from the opening of the liquid blocking structure 63 to prevent the liquid-full probe 62 from generating the liquid-full signal incorrectly. The quantity of liquid blocking structures 63 may match the quantity of liquid-full probes 62. In a specific embodiment of the present invention, the liquid blocking structure 63 comprises a first liquid blocking structure 631 surrounding the first liquid-full probe 621 and a second liquid blocking structure 632 surrounding the second liquid-full probe 622. As shown in FIG. 5B, a first opening 6310 of the first liquid blocking structure 631 and a second opening 6320 of the second liquid blocking structure 632 respectively face the first side wall 601 and the second side wall 602 of the canister 60.

As shown in FIG. 5A and FIG. 5B, when the negative pressure wound therapy device 1 is tilted forwards, the first side wall 601 is located above. Because the first liquid blocking structure 631 only has a first opening 6310 facing the first side wall 601, there must be enough liquid in the canister 60 to contact the first liquid-full probe 621 via the first opening 6310 of the first liquid blocking structure 631. As shown in FIG. 5C and FIG. 5D, when the negative pressure wound therapy device 1 is tilted backwards, the second side wall 602 is located above. Because the second liquid blocking structure 632 only has a second opening 6320 facing the second side wall 602, there must be enough liquid in the canister 60 to contact the second liquid-full probe 622 via the second opening 6320 of the second liquid blocking structure 632. Therefore, regardless of the direction in which the negative pressure wound therapy device 1 is tilted, there must be enough liquid in the canister 60 over the first opening 6310 or the second opening 6320 above and thus the liquid may simultaneously contact the first liquid-full probe 621 and the second liquid-full probe 622 to generate the liquid-full signal to the control circuit board 20, to reduce misjudgment.

In addition, in order to reduce the fluidity of the liquid aspirated in the canister 60, an adsorption solidification member (not shown in the figure) may be disposed in the canister 60, wherein the adsorption solidification member comprises an adsorption material which may achieve an effect of absorbing water or other liquid. It is noted that the adsorption solidification member may not contain activated carbon. As shown in FIG. 4, a partition plate 64 is disposed at the bottom in the canister 60 to limit the movement range of the adsorption solidification member. In a specific embodiment of the present invention, the canister 60 has two partition plates 64 parallel to each other, so that the adsorption solidification member is disposed between the two partition plates 64.

Please refer to FIG. 2. The power device 50 is disposed in the housing 10, so that the negative pressure wound therapy device 1 may be carried by the user without an external power supply. In a specific embodiment of the present invention, the power device 50 is a rechargeable battery which may be a lithium battery, a nickel metal hydride battery or other battery as demanded. In the embodiment as shown in FIG. 2, the power device 50 is removable, and may be removed from the housing 10 and replaced.

In a specific embodiment of the present invention, the negative pressure wound therapy device 1 mainly nurses a patient at home to allow the patient to use the negative pressure wound therapy device 1 in a disposable manner because the price of the negative pressure wound therapy device is affordable. The negative pressure wound therapy device 1 of the present invention can accelerate wound healing, reduce edemas, promote forming of granulation tissues, remove infection and pus, and effectively assist in wound healing. The disposable negative pressure wound therapy device 1 is applied to various acute and chronic wounds, operative wounds, burns/scalds, ulcers (caused by diabetes or unsmooth blood flow) and the like.

A negative pressure wound therapy system of the present invention comprises, for example, the negative pressure wound therapy device 1 and the dressing 2 connected with the negative pressure wound therapy device 1. The dressing 2 is used for covering a wound.

A negative pressure wound therapy method using the negative pressure wound therapy device of the present invention comprises: providing the negative pressure wound therapy device 1; connecting the dressing 2 to the dressing end of the negative pressure wound therapy device 1; covering the wound with the dressing 2; and setting an operating parameter and an operating mode of the negative pressure wound therapy device 1 according to practical usage demands. After being set by a user operation, the dressing 2 connected with the negative pressure wound therapy device 1 is actuated at the wound, thereby achieving a negative pressure therapy effect. See FIG. 1. When a user operates the negative pressure wound therapy device 1, various operating parameters and operating modes may be set. For example, the negative pressure wound therapy device 1 provides an adjustable negative pressure value such as −75 mmHg and −125 mmHg, and an appropriate negative pressure value may be adjusted by pressing the pressure button 101 according to the situation of a wound of the user. The negative pressure wound therapy device 1 may provide two therapy modes, namely, a continuous therapy mode and an intermittent therapy mode, which may be selected by using the mode selection button 102. Under the continuous therapy mode, the negative pressure value remains constant. For example, the negative pressure value continuously remains −75 mmHg or −125 mmHg. Under the intermittent therapy mode, a therapy cycling for 7 minutes is provided. For example, the negative value of the therapy within the first 5 minutes is −75 mmHg or −125 mmHg, the negative value of the therapy within the last 2 minutes is −35 mmHg, and the cycle is maintained.

In addition, in order to prevent the user from contacting a button incorrectly, after being started, the negative pressure wound therapy device 1 will automatically enter a locked mode within 30 s, so as to prevent incorrect contact from the patient affecting operation of the device and to reducing the effect of therapy. If the patient desires to unlock the negative pressure wound therapy device, the patient may continuously and quickly press the standby button 104 twice within 3 s so as to unlock the negative pressure wound therapy device.

Moreover, the negative pressure wound therapy device 1 allows the user to enquire the number of remaining days that the device is available. Under the locked mode, the user presses the pressure button 101 down to know the number of remaining days that the device is available according to the flickering frequency of the pressure indicator light 1010. For example, when the pressure indicator light 1010 flickers five times, it indicates that the device is available for five days.

The negative pressure wound therapy device 1 provides battery indication to allow the user to clearly know the state of the device. During booting, the power indicator light 1030 is on all the time. In the case of low battery, the power indicator light 1030 will flicker to remind the user that the battery is low. In addition, when the canister 60 is full of liquid or air leaks from the device, the negative pressure wound therapy device 1 may present an alarm. In this case, the standby indicator light 1040 will be turned on, and the negative pressure wound therapy device 1 will present an alarm to notify the user to check for air leakage or the quantity of liquid in the canister 60.

Figure 6A:
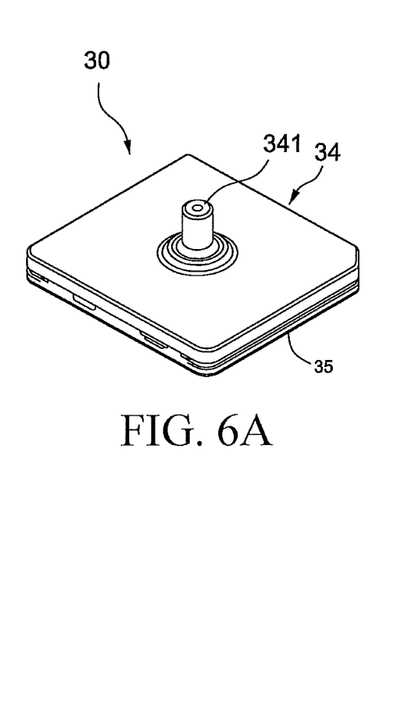
FIG. 6A is a perspective view of a pump of the present invention.
Figure 6B:
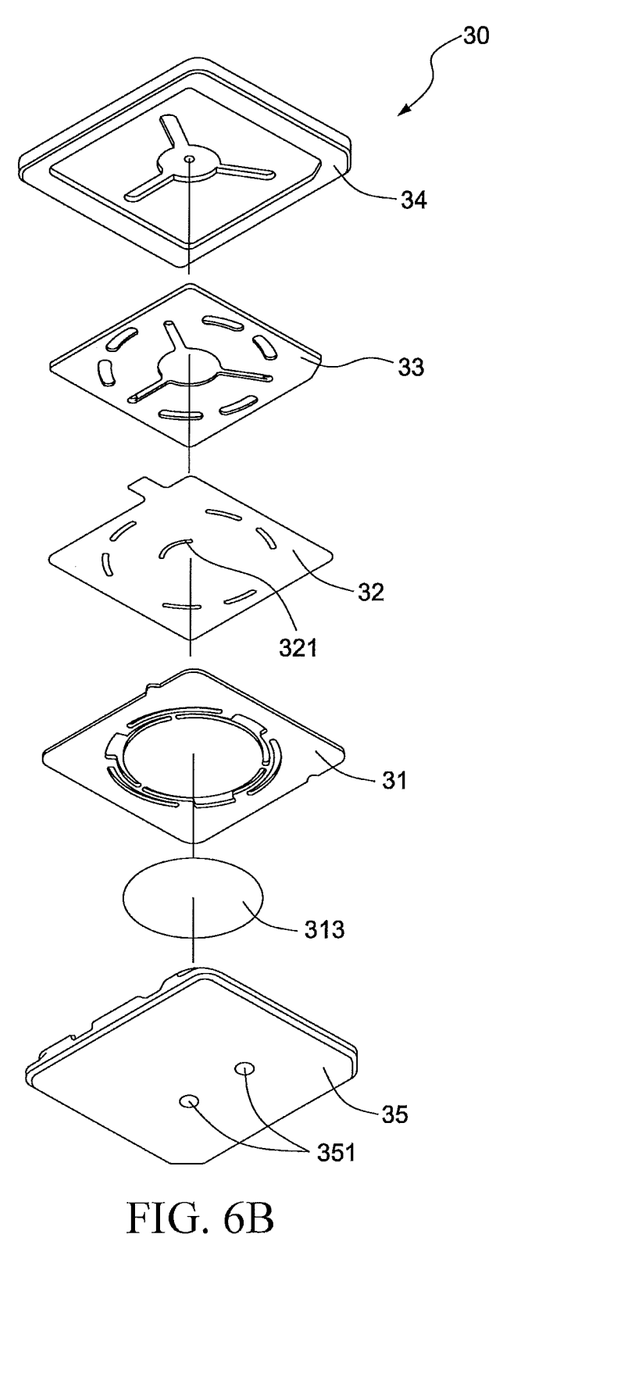
FIG. 6B is an exploded view of a pump of the present invention.

Please refer to FIG. 6A and FIG. 6B. FIG. 6A is a perspective view of a pump used in a specific embodiment of the present invention. FIG. 6B is an exploded view of a pump used in a specific embodiment of the present invention. The pump 30 of the present invention comprises an aspiration cover plate 34 disposed outside and a back plate 35 combinable with the aspiration cover plate 34. The aspiration cover plate 34 comprises a connector 341, protruding from the surface of the aspiration cover plate 34 for connecting the aspiration conduit 40 and defining the aspiration end of the pump 30. The center of the connector 341 is provided with an air inlet for guiding fluid into the pump 30 via the aspiration conduit 40 and the connector 341. The back plate 35 covers a vibrating sheet 31 and a voltage-actuated deformation element 313 thereof. The back plate 35 has an air outlet 351 for discharging fluid and defining the discharge end of the pump 30. In addition, the voltage-actuated deformation element 313, the vibrating sheet 31, a flap valve 32 and a flow guide member 33 are disposed inside the pump 30 sequentially along a direction from the back plate 35 to the aspiration cover plate 34, wherein the voltage-actuated deformation element 313 (such as piezoelectric vibration element) is attached to the surface, facing the back plate 35, of the vibrating sheet 31. It is noted that in order to make the fluid pass through the flap valve 32 more smoothly, in the pump used in a specific embodiment of the present invention, a through slot 321 is a non-linear through slot as shown in FIG. 6B. Compared with a round or linear through slot, the non-linear through slot 321 has the advantages that when the fluid passes through the non-linear through slot 321, a part, near the non-linear through slot 321, of the flap valve 32 will be opened to enlarge an air vent, so that the area of the fluid passing through the flap valve 32 will be larger than the area of the non-linear through slot 321. In addition, because sound generated during operation of the pump 30 lies beyond the frequency range detected by the human ear, the pump 30 of the present invention is a silent pump.

Figure 7:
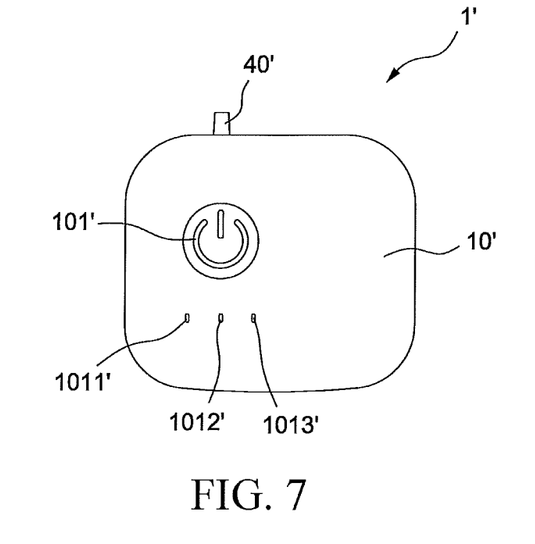
FIG. 7 is a front view of another embodiment for a negative pressure wound therapy device of the present invention.
Figure 8:
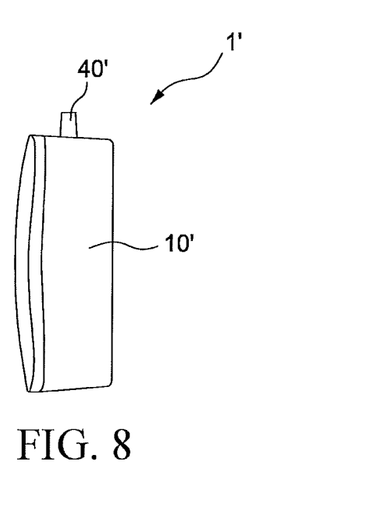
FIG. 8 is a right view of another embodiment for a negative pressure wound therapy device of the present invention.
Figure 9:
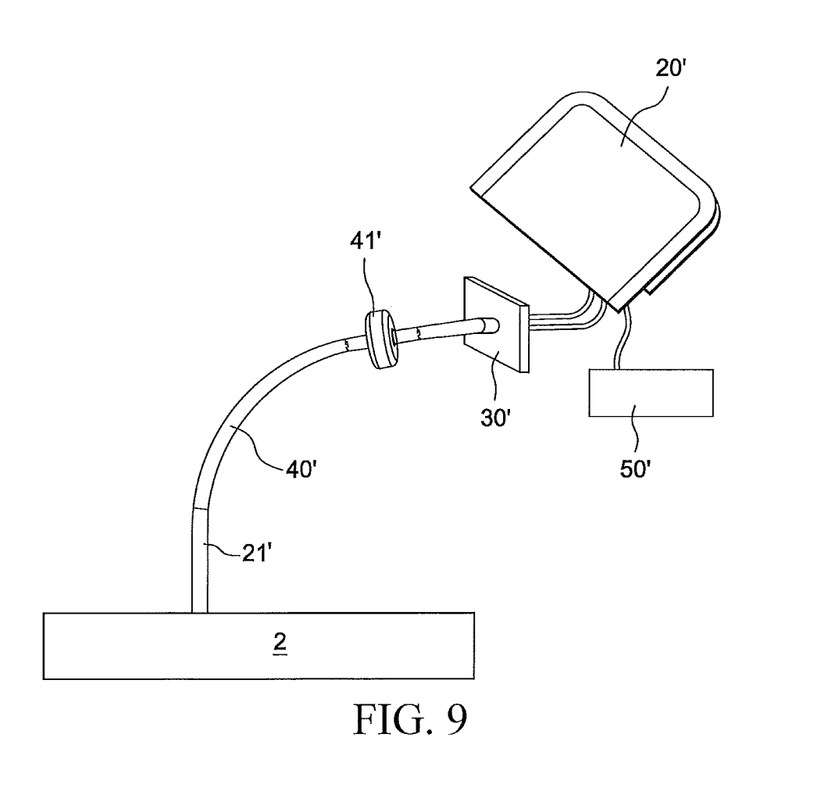
FIG. 9 is an exploded view displaying main internal elements in another embodiment for a negative pressure wound therapy device of the present invention.

Please refer to FIG. 7, FIG. 8 and FIG. 9. FIG. 7 is a front view of another embodiment for a negative pressure wound therapy device 1' of the present invention. FIG. 8 is a right view of another embodiment for a negative pressure wound therapy device 1' of the present invention. FIG. 9 is an exploded view displaying main internal elements in another embodiment for a negative pressure wound therapy device 1' of the present invention. The negative pressure wound therapy device 1' comprises a housing 10', a control circuit board 20', a pump 30', an aspiration conduit 40', and a power device 50'. Compared with the previous embodiment, the negative pressure wound therapy device 1' of the present embodiment does not comprise a canister 60 and a snuffle valve 42. A silent pump as shown in FIG. 6A and FIG. 6B may be adopted to reduce machine-generated sound, to achieve a soundless state, and to achieve a silencing effect in a process that uses it.

As shown in FIG. 9, the pump 30' is disposed in the housing 10', and is electrically connected with the control circuit board 20' disposed in the housing 10'. The pump 30' defines an aspiration end and a discharge end in the direction of fluid flow. The pump 30' discharges the fluid from the aspiration end to the discharge end to generate negative pressure at the aspiration end.

The aspiration conduit 40' has a pump end and a dressing end, wherein the pump end of the aspiration conduit 40' is fluidly connected to the aspiration end of the pump 30', and the dressing end of the aspiration conduit 40' is fluidly connected to a dressing 2 used for covering a wound via a dressing conduit 21'. In a specific embodiment of the present invention, the aspiration conduit 40' comprises a check valve 41' disposed between the pump end and the dressing end. The check valve 41' prevents fluid such as air from flowing to the dressing end from the pump end of the aspiration conduit 40'.

As shown in FIG. 7 and FIG. 8, buttons and indicator lights are disposed on the surface of the housing 10', and are electrically connected to the control circuit board 20', respectively. In a specific embodiment of the present invention, a power button 101' is disposed on the front surface of the housing 10', and three indicator lights 1011', 1012', 1013', namely a green light, an orange light and a red light, are disposed below the power button 101'. In addition, in a specific embodiment of the present invention, the power button 101' may be, for example, a touch switch, capable of effectively operating a machine. The housing 10' is made water-resistant by glue; it not only has a waterproof effect, but also can be conveniently used while taking a bath for convenience. In other embodiments of the present invention, a waterproof rubber gasket is disposed at a gap of the housing 10' to increase the tightness of the housing 10', thereby enhancing the waterproof effect.

In addition, a negative pressure value of the negative pressure wound therapy device 1' is preset as −125 mmHg. Under this negative pressure value, the pus from the wound at the dressing 2 will not be aspirated by the pump 30' into the aspiration conduit 40' to enter the check valve 41'. In addition, the negative pressure wound therapy device 1' provides a continuous therapy mode, so the negative pressure value remains constant at −125 mmHg.

The negative pressure wound therapy device 1' provides a battery indication to clearly show the user the state of the device. During booting, the indicator light 1011' flickers, and when the device enters continuous therapy mode, the indicator light 1011' is on all the time. In the case of low battery, the indicator light 1013' will flicker to remind the user that the battery is low. In addition, when air leaks from the device to cause negative pressure shortage, the negative pressure wound therapy device 1' may present an alarm, and the indicator light 1012' will flicker to remind the user to check for air leakage of the device.

Figure 10:
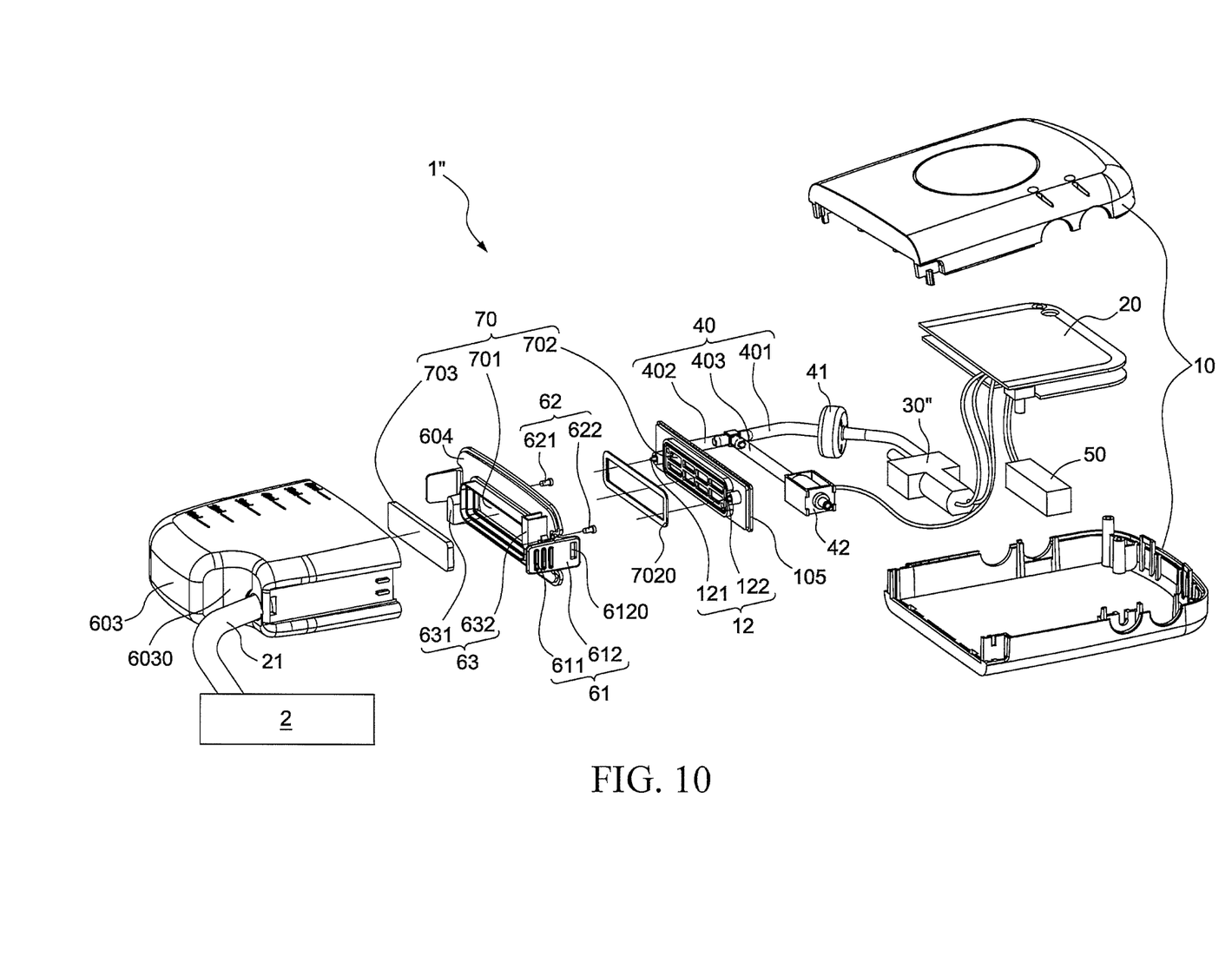
FIG. 10 is an exploded view displaying main internal elements in a further embodiment for a negative pressure wound therapy device of the present invention.

Please refer to FIG. 10. FIG. 10 is an exploded view displaying main internal elements in a further embodiment for a negative pressure wound therapy device 1" of the present invention. The negative pressure therapy principle of the negative pressure wound therapy device 1" is roughly the same as the negative pressure therapy principle of the negative pressure wound therapy device 1 as shown in FIG. 2, and comprises a housing 10, a control circuit board 20, a pump 30", an aspiration conduit 40, a power device 50, and a canister 60. However, a micro-motor pump is adopted as the pump 30" of the negative pressure wound therapy device 1". Other structures of the negative pressure wound therapy device 1" in this embodiment are identical or similar to those of the negative pressure wound therapy device 1 as shown in FIG. 1A to FIG. 5B, and will not be repeated herein.

The foregoing embodiments may also be slightly modified according to the spirit of the present invention. Moreover, fine modifications meeting the spirit of the present invention fall within the scope of protection of the present invention. Therefore, the embodiments mentioned above should be exemplary, not restrictive.

The above-described embodiments of the present invention are intended to be illustrative only. Numerous alternative embodiments may be devised by persons skilled in the art without departing from the scope of the following claims.

What is claimed is:

1. A negative pressure wound therapy (NPWT) device connected with a dressing, comprising:
   a housing;
   a control circuit board disposed in the housing;
   a pump disposed in the housing and comprising a discharge end and an aspiration end, wherein the pump discharges fluid from the discharge end to generate negative pressure at the aspiration end, and the pump further comprises a voltage-actuated deformation element to push the fluid from the aspiration end to the discharge end; and
   an aspiration conduit having a pump end and a dressing end, wherein the pump end is fluidly connected to the aspiration end of the pump, and the dressing end is fluidly connected to the dressing used for covering a wound,
   wherein the control circuit board controls the pump to generate the negative pressure in the aspiration conduit, and applies negative pressure to the wound covered by the dressing via the aspiration conduit;
   a canister for storing a liquid aspirated from the wound, wherein the canister has a top for engaging with the housing, and has a first end for connecting with the dressing end of the aspiration conduit and a second end for connecting with a dressing conduit of the dressing, the canister comprises a first liquid-full probe adjacent to a first side wall of the canister and a second liquid-full probe adjacent to a second side wall of the canister opposite to the first side wall wherein the first and second liquid-full probes extend inwardly from a top wall of the canister;
   wherein the canister further comprises:
   a first liquid blocking structure surrounding the first liquid-full probe and only having a first opening facing the first side wall of the canister, such that there must be enough liquid in the canister to contact the first liquid-full probe via the first opening of the first liquid blocking structure; and
   a second liquid blocking structure surrounding the second liquid-full probe and only having a second opening facing the second side wall of the canister, such that there must be enough liquid in the canister to contact the second liquid-full probe via the second opening of the second liquid blocking structure;
   wherein the first opening and the second opening open in opposite directions, wherein the liquid simultaneously contacts the first liquid-full probe and the second liquid-full probe to generate a liquid-full signal to the control circuit board to reduce misjudgment.

2. The negative pressure wound therapy device according to claim 1, wherein the first liquid-full probe and the second liquid-full probe are electrically conductive to each other to generate the liquid-full signal when the first liquid-full probe and the second liquid-full probe simultaneously contact the liquid.

3. The negative pressure wound therapy device according to claim 1, wherein the negative pressure wound therapy device further comprises a first terminal and a second terminal disposed at the bottom of the housing, and the first terminal and the second terminal electrically connect the first liquid-full probe and the second liquid-full probe to the control circuit board respectively.

4. The negative pressure wound therapy device according to claim 1, wherein the aspiration conduit comprises a check valve disposed between the pump end and the dressing end of the aspiration conduit, and the check valve prevents the fluid from flowing to the dressing end from the pump end of the aspiration conduit.

5. The negative pressure wound therapy device according to claim 4, wherein the negative pressure wound therapy device further comprises a snuffle valve, and the aspiration conduit comprises a tee conduit with a first end, a second end and a third end, the first end of the tee conduit is fluidly connected to the check valve, the second end of the tee conduit is fluidly connected to the dressing end of the aspiration conduit, the third end of the tee conduit is fluidly connected to the snuffle valve, and the snuffle valve is controlled by the control circuit board to release the negative pressure in the aspiration conduit.

6. The negative pressure wound therapy device according to claim 1, wherein the housing is water-resistant.

7. The negative pressure wound therapy device according to claim 1, wherein the sound generated during the operation of the pump lies beyond the frequency range detected by the human ear, and the pump is a silent pump.

8. A negative pressure wound therapy system, comprising the negative pressure wound therapy device according to claim 7 and the dressing connected with the negative pressure wound therapy device, wherein the dressing is used for covering the wound.

9. A negative pressure wound therapy method, comprising:
   providing the negative pressure wound therapy device according to claim 7;
   connecting the dressing to the dressing end of the negative pressure wound therapy device;
   covering the wound with the dressing; and
   setting an operating parameter and an operating mode of the negative pressure wound therapy device.

* * * * *